US011426060B2

(12) United States Patent
Takata (10) Patent No.: US 11,426,060 B2
(45) Date of Patent: Aug. 30, 2022

(54) OPTICAL SCANNING ENDOSCOPE DEVICE

(71) Applicant: OLYMPUS CORPORATION, Tokyo (JP)

(72) Inventor: Yuhei Takata, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 669 days.

(21) Appl. No.: 16/406,149

(22) Filed: May 8, 2019

(65) Prior Publication Data

US 2019/0261837 A1 Aug. 29, 2019

Related U.S. Application Data

(63) Continuation of application No. PCT/JP2016/086882, filed on Dec. 12, 2016.

(51) Int. Cl.
*A61B 1/00* (2006.01)
*G02B 23/24* (2006.01)
(Continued)

(52) U.S. Cl.
CPC ............ *A61B 1/00172* (2013.01); *A61B 1/00* (2013.01); *A61B 1/04* (2013.01); *A61B 1/045* (2013.01);
(Continued)

(58) Field of Classification Search
CPC ... A61B 1/00172; A61B 1/045; A61B 1/0669; G02B 23/2469; G02B 23/26; G02B 26/103
See application file for complete search history.

(56) References Cited

U.S. PATENT DOCUMENTS 4,622,584 A * 11/1986 Nagasaki .................. A61B 1/05
348/687
2005/0099824 A1* 5/2005 Dowling .............. A61B 1/0653
362/572
(Continued)

FOREIGN PATENT DOCUMENTS

EP 3114984 A1 1/2017
JP 2011-255015 A 12/2011
(Continued)

OTHER PUBLICATIONS

International Search Report dated Mar. 7, 2017 issued in PCT/JP2016/086882.

*Primary Examiner* — Alexandra L Newton
*Assistant Examiner* — Shankar Raj Ghimire
(74) *Attorney, Agent, or Firm* — Scully, Scott, Murphy & Presser, P.C.

(57) ABSTRACT

An optical scanning endoscope device includes: a laser element; an optical fiber that guides laser light from the laser element; a first detector that detects a guided light amount of the laser light in the optical fiber; a second detector that detects light from a subject and outputs a detection signal; a first calculator that calculates an optical coupling ratio between the laser element and the optical fiber on the basis of the guided light amount; a second calculator that calculates a degradation ratio of the laser element on the basis of the guided light amount; a first adjuster that adjusts the magnitude of the detection signal on the basis of the optical coupling ratio; and a second adjuster that adjusts the output light amount of the laser light from the laser element on the basis of the degradation ratio.

6 Claims, 8 Drawing Sheets

(51) Int. Cl.
*A61B 1/045* (2006.01)
*A61B 1/06* (2006.01)
*G02B 23/26* (2006.01)
*G02B 26/10* (2006.01)
*A61B 1/04* (2006.01)

(52) U.S. Cl.
CPC .............. *A61B 1/06* (2013.01); *A61B 1/0669* (2013.01); *G02B 23/2469* (2013.01); *G02B 23/26* (2013.01); *G02B 26/103* (2013.01)

(56) References Cited

U.S. PATENT DOCUMENTS

| | | | | |
|---|---|---|---|---|
| 2006/0028155 A1* | 2/2006 | Young | .................... | H05B 45/58 315/308 |
| 2010/0123775 A1* | 5/2010 | Shibasaki | ............ | H04N 5/2354 348/68 |
| 2013/0154509 A1* | 6/2013 | Yabe | .................... | A61B 1/0669 315/297 |
| 2014/0332677 A1* | 11/2014 | Fujiwara | ................ | A61B 1/063 250/234 |
| 2016/0150948 A1* | 6/2016 | Shimamoto | .............. | A61B 1/07 600/109 |
| 2016/0313551 A1* | 10/2016 | Takei | ................. | G02B 23/2469 |
| 2017/0007097 A1* | 1/2017 | Takei | ....................... | A61B 1/07 |
| 2017/0027426 A1* | 2/2017 | Takei | ....................... | A61B 1/07 |

FOREIGN PATENT DOCUMENTS

| | | | | |
|---|---|---|---|---|
| JP | 2013-027432 A | 2/2013 | | |
| JP | 2013-099458 A | 5/2013 | | |
| JP | 2015-019816 A | 2/2015 | | |
| JP | 5974206 B2 | 8/2016 | | |
| WO | WO-2016027484 A1 * | 2/2016 | ......... | A61B 1/00059 |

* cited by examiner

OPTICAL SCANNING ENDOSCOPE DEVICE

CROSS-REFERENCE TO RELATED APPLICATIONS

This is a continuation of International Application PCT/JP2016/086882 which is hereby incorporated by reference herein in its entirety.

TECHNICAL FIELD

The present invention relates to an optical scanning endoscope device.

BACKGROUND ART

Heretofore, there is known an optical scanning endoscope device that includes an optical fiber that guides laser light from a light source and scans laser light emitted from the optical fiber by making the optical fiber vibrate (for example, refer to PTL 1). The emitted light amount of laser light emitted from the optical fiber is reduced by changes that occur in the use environment such as the surrounding temperature. In PTL 1, the output light amount of the light source is adjusted such that the emitted light amount emitted from the optical fiber is constant.

CITATION LIST

Patent Literature

PTL 1: Japanese Unexamined Patent Application Publication No. 2011-255015

SUMMARY OF INVENTION

An aspect of the present invention provides an optical scanning endoscope device that includes: a laser element that outputs laser light; an optical fiber that guides the laser light output from the laser element and emits the laser light toward a subject; a first detector that detects a guided light amount of the laser light guided by the optical fiber; a second detector that detects light generated at the subject due to radiation of the laser light and outputs a detection signal; a first calculator that calculates an optical coupling ratio between the laser element and the optical fiber on the basis of the guided light amount detected by the first detector; a second calculator that calculates a degradation ratio of the laser element on the basis of the guided light amount detected by the first detector; a first adjuster that adjusts a magnitude of the detection signal on the basis of the optical coupling ratio calculated by the first calculator; and a second adjuster that adjusts an output light amount of the laser light output from the laser element on the basis of the degradation ratio calculated by the second calculator.

DESCRIPTION OF EMBODIMENTS

An optical scanning endoscope device 1 according to an embodiment of the present invention will be described while referring to the drawings.

Figure 1:
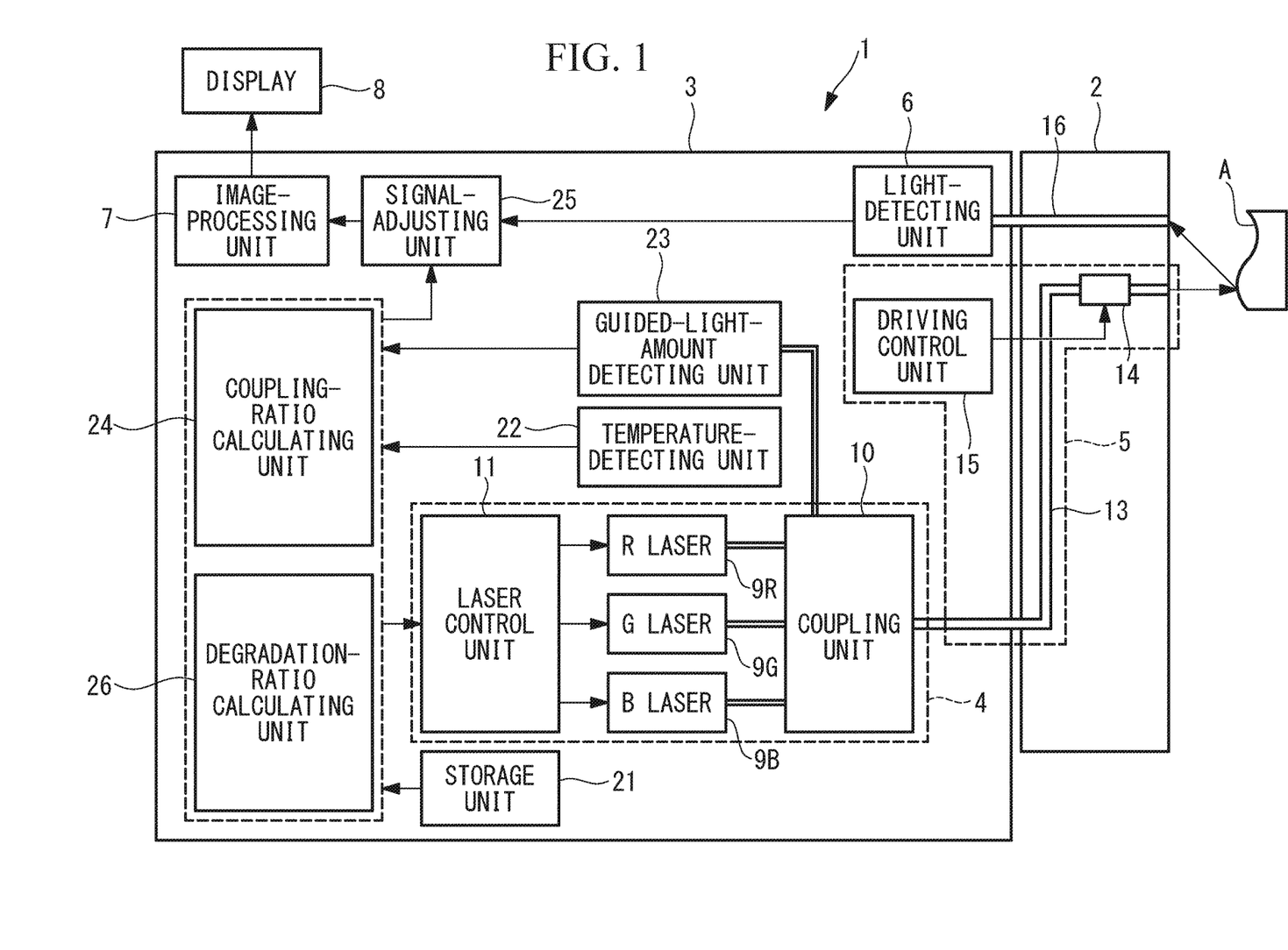
FIG. 1 is an overall configuration diagram of an optical scanning endoscope device according to an embodiment of the present invention.

As illustrated in FIG. 1, the optical scanning endoscope device 1 according to this embodiment includes a long thin scope 2 that is to be inserted into the inside of a body, and a casing 3 that is connected to a base end of the scope 2. The optical scanning endoscope device 1 further includes: a light source unit 4 that outputs laser light; an optical scanning unit 5 that includes an optical fiber 13 and radiates laser light emitted from the optical fiber 13 onto a subject A while scanning the laser light; a light-detecting unit 6 that detects scattered light out of laser light from the subject A; and an image-processing unit 7 that forms an image of the subject A. The light source unit 4, the light-detecting unit 6, and the image-processing unit 7 are provided inside the casing 3, and the optical scanning unit 5 is provided so as to straddle the scope 2 and the casing 3. A display 8, which is for displaying an image generated by the image-processing unit 7, is connected to the casing 3.

The light source unit 4 includes three laser elements 9R, 9G, and 9B, which respectively output red (R), green (G), and blue (B) laser light, a coupling unit 10 that optically couples the three laser elements 9R, 9G, and 9B and an incident end, which is the base end, of the optical fiber 13; and a laser control unit 11 that controls the laser elements 9R, 9G, and 9B.

Figure 2:
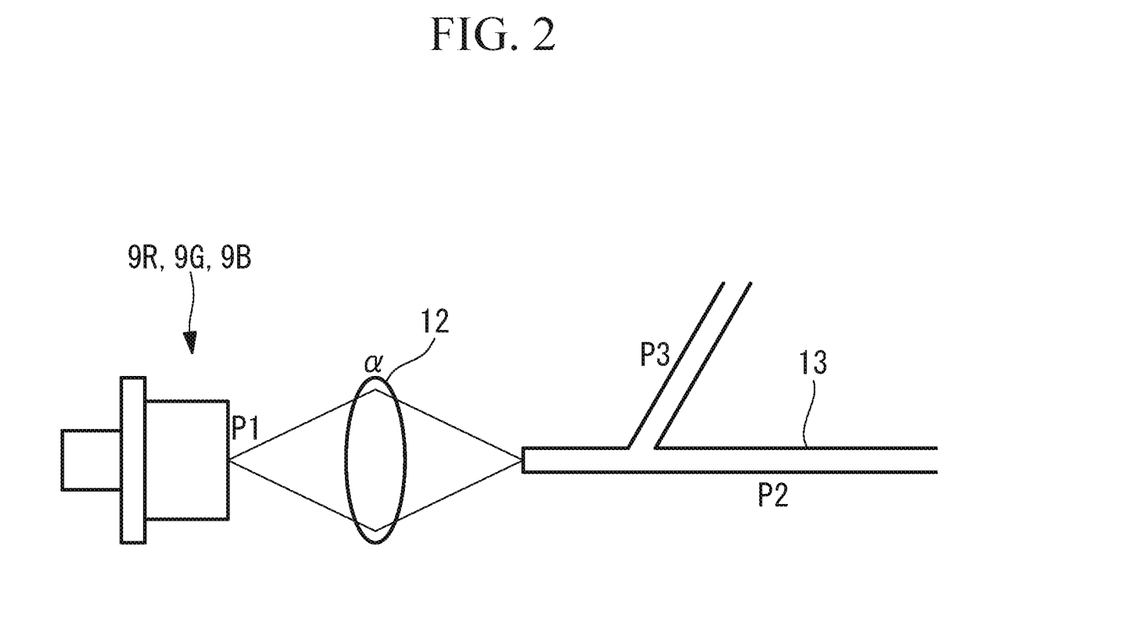
FIG. 2 is a diagram for explaining optical coupling between laser elements and an optical fiber in a coupling unit in FIG. 1.

FIG. 2 is a diagram that schematically illustrates optical coupling of the laser elements 9R, 9G, and 9B and the incident end of the optical fiber 13 in the coupling unit 10. Each of the three laser elements 9R, 9G, and 9B and the incident end of the optical fiber 13 are optically coupled with each other by a coupling element 12 such as a lens and the laser light beams output from the laser elements 9R, 9G, and 9B are incident on the incident end of the optical fiber 13.

The laser control unit 11 makes the laser elements 9R, 9G, and 9B light up in a pulsed manner in a prescribed order. Therefore, the R, G, and B laser light beams are incident on the optical fiber 13 in a prescribed order and the R, G, and B laser light beams are radiated onto the subject A in the prescribed order. Furthermore, the laser control unit (output-light-amount adjusting unit) 11 controls the laser elements 9R, 9G, and 9B so as to increase an output light amount by increasing a driving current supplied to the laser elements 9R, 9G, and 9B when a reduction in the output light amount occurs due to degradation of the laser elements 9R, 9G, and 9B over time, as will be described in detail later.

The laser elements 9R, 9G, and 9B may be individually provided with temperature control elements such as Peltier elements for controlling the temperatures of the laser elements 9R, 9G, and 9B so as to be constant with the aim of stabilizing the light amounts and wavelengths of the laser light beams and extending the lifespans of the laser elements 9R, 9G, and 9B.

The optical scanning unit 5 includes the radiating optical fiber 13 and an actuator 14, which are arranged inside the scope 2, and a driving control unit 15 that is arranged inside the casing 3 and controls driving of the actuator 14.

The optical fiber 13 is a single mode fiber. The optical fiber 13 is arranged along a longitudinal direction inside the scope 2 and a base end of the optical fiber 13 is connected to the coupling unit 10. The optical fiber 13 guides laser light supplied thereto from the coupling unit 10 and emits from an emission end thereof, which is the leading end thereof, the laser light toward the subject A, which faces the leading end surface of the scope 2.

The actuator 14 is, for example, a piezoelectric actuator including a piezoelectric element or an electromagnetic actuator including an electromagnetic coil, and is attached to the leading end of the optical fiber 13. The actuator 14 scans the laser light emitted from the leading end of the optical fiber 13 by making the leading end of the optical fiber 13 vibrate in accordance with a driving signal supplied from the driving control unit 15.

The light-detecting unit 6 includes a high-sensitivity light detector (not illustrated) such as an avalanche photo diode (APD) or a photo multiplier tube. The light-detecting unit 6 receives scattered light of the laser light via a reception optical fiber 16 that is provided in the scope 2. The optical fiber 16 is a multi-mode fiber and extends from a leading end of the scope 2 to the light-detecting unit 6. The light-detecting unit 6 detects the scattered light from the optical fiber 16 using the light detector, acquires a detection signal representing the intensity of the scattered light, and transmits the acquired detection signal to the image-processing unit 7 via a signal-adjusting unit 25, which will be described later.

The image-processing unit 7 forms a two-dimensional image of the subject A by receiving information regarding the radiation positions of the laser light along a scanning track from the driving control unit 15 and associating detection signals from the light-detecting unit 6 with the radiation positions. The formed image is transmitted to the display 8 and displayed on the display 8. The image-processing unit 7 may subject the image to image processing such as white balance adjustment, brightness adjustment, color correction, and gamma correction.

As illustrated in FIG. 1, inside the casing 3, the optical scanning endoscope device 1 further includes: a storage unit 21 that stores characteristic optical values at the time of shipping; a temperature-detecting unit 22 that detects the surrounding temperature of the light source unit 4; a guided-light-amount detecting unit 23 that detects a light amount of the laser light guided by the optical fiber 13; a coupling-ratio calculating unit 24 that calculates an optical coupling ratio $\alpha$ between the laser elements 9R, 9G, and 9B and the incident end of the optical fiber 13; the signal-adjusting unit 25 that adjusts the magnitude of a detection signal; and a degradation-ratio calculating unit 26 that calculates a degradation ratio of the laser elements 9R, 9G, and 9B.

Here, an emitted light amount of laser light emitted from the leading end of the optical fiber 13 toward the subject A will be described.

The emitted light amount is determined in accordance with the output light amount of laser light from the laser elements 9R, 9G, and 9B and the optical coupling ratio $\alpha$ between the laser elements 9R, 9G, and 9B and the incident end of the optical fiber 13.

The output light amount of the laser elements 9R, 9G, and 9B gradually decreases with degradation over time in accordance with the total use time of the laser elements 9R, 9G, and 9B.

The optical coupling ratio $\alpha$ changes in accordance with changes in the surrounding temperature of the light source unit 4. Specifically, the core diameter of the optical fiber 13 used in the optical scanning endoscope device 1 is very small at around 2.5 μm or less. Therefore, the central axis of the optical fiber 13 is displaced relative to the optical axis of the laser light from the laser elements 9R, 9G, and 9B due to slight thermal expansion of the metal constituting a member holding the optical fiber 13. Therefore, the optical coupling ratio $\alpha$ changes and the emitted light amount from the optical fiber 13 also changes when the surrounding temperature changes. For example, when the surrounding temperature changes by ±15° C. with respect to 25° C., there is a change of around 20% at maximum in the emitted light amount of laser light.

Figure 3:
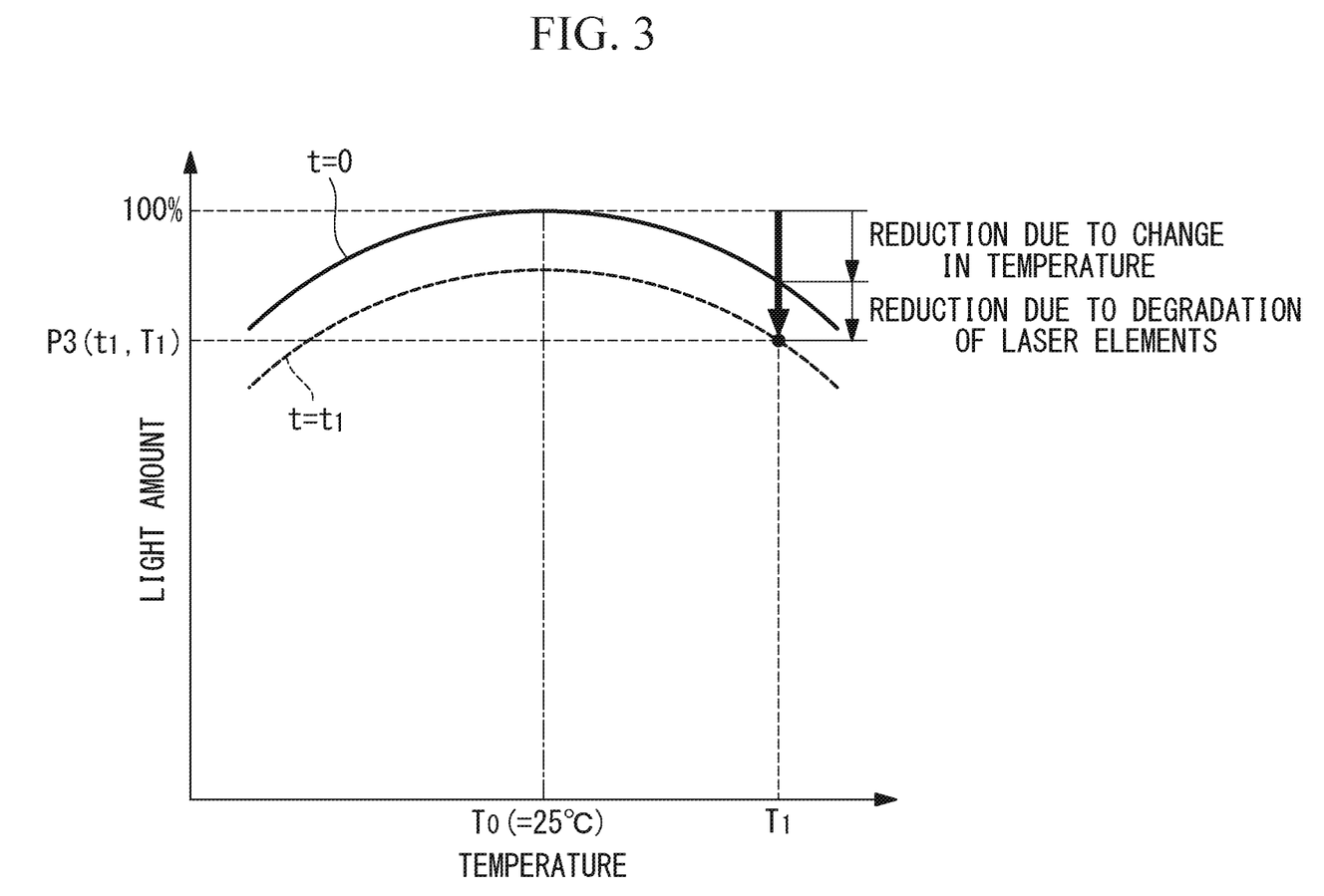
FIG. 3 is a graph illustrating the relationship between a detected light amount detected by a guided-light-amount detecting unit and the surrounding temperature at the time of shipping (solid line) and after a reduction caused by degradation over time (broken line).

FIG. 3 illustrates an example of the relationship between the surrounding temperature and a detected light amount (guided light amount) P3 detected by the guided-light-amount detecting unit 23. As illustrated in FIG. 2, part of the laser light incident on the optical fiber 13 from the laser elements 9R, 9G, and 9B is split at a prescribed splitting ratio m from the optical fiber 13 at the base end of the optical fiber 13 and guided to the guided-light-amount detecting unit 23 and the remaining part of the laser light is emitted from the leading end of the optical fiber 13. Therefore, a change in an emitted light amount P2 can be detected from the detected light amount P3.

Generally, the optical scanning endoscope device 1 is manufactured such that the optical coupling ratio $\alpha$ is maximum at a prescribed reference temperature $T_0$ (for example, 25° C.). Therefore, the detected light amount P3 decreases as the surrounding temperature increases or decreases from the reference temperature $T_0$.

Describing this in more detail while referring to FIG. 2, the following Formulas (1) and (2) hold true between an output light amount P1 from the laser elements 9R, 9G, and 9B, the emitted light amount P2, and the detected light amount P3.

$$\alpha \times P1 = P2 + P3 \quad (1)$$

$$m = P3/(P2+P3) \quad (2)$$

Formula (3) is obtained from Formulas (1) and (2).

$$P3 = m \times \alpha \times P1 \quad (3)$$

The optical coupling ratio $\alpha$ depends on a surrounding temperature T, the output light amount P1 depends on the total use time t, and the detected light amount P3 depends on both the surrounding temperature T and the total use time t. Therefore, the optical coupling ratio, the output light amount, and the detected light amount at the surrounding temperature T and the total use time t are respectively represented by $\alpha(T)$, $P1(t)$, and $P3(t, T)$.

The change ratio of the optical coupling ratio $\alpha(T_1)$ at the surrounding temperature T with respect to the optical coupling ratio $\alpha(T_0)$ at the reference temperature $T_0$ is expressed by $\alpha(T_1)/\alpha(T_0)$.

The detected light amount P3 (0, $T_0$) at the reference temperature $T_0$ when the total use time t=0 (i.e., at the time of shipping) is expressed by Formula (4) below.

$$P3(0,T_0)=m\times\alpha(T_0)\times P1(0) \quad (4)$$

The detected light amount P3 ($t_1$, $T_1$) at the surrounding temperature $T_1$ at the total use time $t_1$ is expressed by Formula (5) below.

$$P3(t_1,T_0)=m\times\alpha(T_2)\times P1(t_1) \quad (5)$$

Therefore, when the degradation ratio of the laser elements 9R, 9G, and 9B is defined as a ratio $P1(t_1)/P1(0)$ of the output light amount at the total use time $t_1$ with respect to the output light amount at the shipping time t=0, the degradation ratio is derived as given below from Formulas (4) and (5).

$$P1(t_1)/P1(0)=\alpha(T_0)/\alpha(T_0)\times P3(t_1,T_1)/P3(0,T_0) \quad (6)$$

As is clear from Formula (6), the degradation ratio $P1(t_1)/P1(0)$, the optical coupling ratio $\alpha(T_1)$, and the detected light amount $P3(t_1, T_1)$ are in a fixed relationship with each other.

The relationship between the surrounding temperature T and the detected light amount P3 measured prior to shipping from the factory (i.e., total use time t=0) (refer to solid line in FIG. 3) is stored in the storage unit 21.

Furthermore, the output light amount P1(0) of the laser elements 9R, 9G, and 9B measured prior to shipping from the factory is stored in the storage unit 21.

Figure 4:
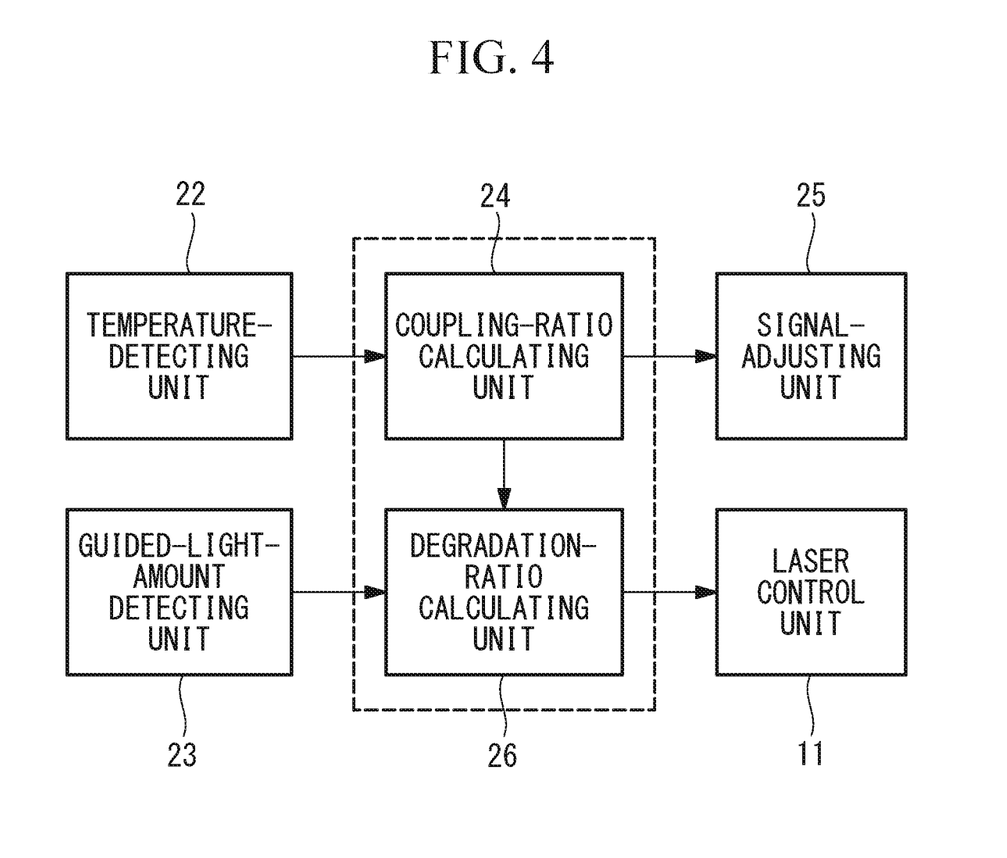
FIG. 4 is a diagram illustrating the flow of signals in the optical scanning endoscope device in FIG. 1.

FIG. 4 illustrates the flow of signals between the temperature-detecting unit 22, the guided-light-amount detecting unit 23, the coupling-ratio calculating unit 24, the signal-adjusting unit 25, the degradation-ratio calculating unit 26, and the laser control unit 11.

The temperature-detecting unit 22 detects the surrounding temperature $T_1$ at the coupling unit 10 or in the vicinity thereof and transmits the detected surrounding temperature $T_1$ to the coupling-ratio calculating unit 24.

As illustrated in FIG. 2, the guided-light-amount detecting unit 23 detects the light amount P3, which is part of the laser light guided by the optical fiber 13, at the base end of the optical fiber 13 and transmits the detected light amount P3 to the degradation-ratio calculating unit 26.

The coupling-ratio calculating unit 24 receives the surrounding temperature $T_1$ from the temperature-detecting unit 22, reads out optical coupling ratios $\alpha(T_0)$ and $\alpha(T_1)$ for the reference temperature $T_0$ and the surrounding temperature $T_1$ from the storage unit 21, calculates a change ratio $\alpha(T_1)/\alpha(T_0)$ of the optical coupling ratio, and transmits the change ratio $\alpha(T_1)/\alpha(T_0)$ to the signal-adjusting unit 25 and the degradation-ratio calculating unit 26.

The signal-adjusting unit 25 multiplies the detection signal received from the light-detecting unit 6 by the reciprocal of the change ratio $\alpha(T_1)/\alpha(T_0)$ and transmits the obtained detection signal to the image-processing unit 7. Thus, when the optical coupling ratio $\alpha(T)$ decreases due to a change in the surrounding temperature and the emitted light amount P2 emitted from the optical fiber 13 decreases, the detection signal is amplified in the signal-adjusting unit 25 in order to compensate for the decrease in the emitted light amount P2.

The degradation-ratio calculating unit 26 receives the detected light amount P3 ($t_1$, $T_1$) from the guided-light-amount detecting unit 23, receives the change ratio $\alpha(T_1)/\alpha(T_0)$ of the optical coupling ratio from the coupling-ratio calculating unit 24, and reads out the initial output light amount P1(0) of the laser elements 9R, 9G, and 9B at the reference temperature $T_0$ from the storage unit 21. Then, the degradation-ratio calculating unit 26 calculates the degradation ratio $P1(t_1)/P1(0)$ of the laser elements 9R, 9G, and 9B from Formula (6) using the detected light amount $P3(t_1, T_1)$, the change ratio $\alpha(T_1)/\alpha(T_0)$, and the output light amount P1(0), and transmits the calculated degradation ratio to the laser control unit 11.

The laser control unit 11 makes the laser elements 9R, 9G, and 9B output laser light by supplying the laser elements 9R, 9G, and 9B with a driving current having an initial value at the time of initiation of control of the laser elements 9R, 9G, and 9B. The initial value of the driving current is decided upon prior to shipping from the factory such that the emitted light amount P2 is an appropriate initial set amount (for example, 5 mW) at the reference temperature $T_0$. The initial value of the driving current is stored, for example, in the storage unit 21 so that the laser control unit 11 is able to acquire the initial value of the driving current when necessary.

After that, the laser control unit 11 multiplies the initial value of the driving current by the reciprocal of the degradation ratio $P1(t_1)/P1(0)$ received from the degradation-ratio calculating unit 26 and changes the value of the driving current supplied to the laser elements 9R, 9G, and 9B to the value of the calculated driving current. Thus, when the output light amount P1 decreases due to degradation of the laser elements 9R, 9G, and 9B, the driving current is increased so as to compensate for the decrease in the output light amount P1.

Figure 5:
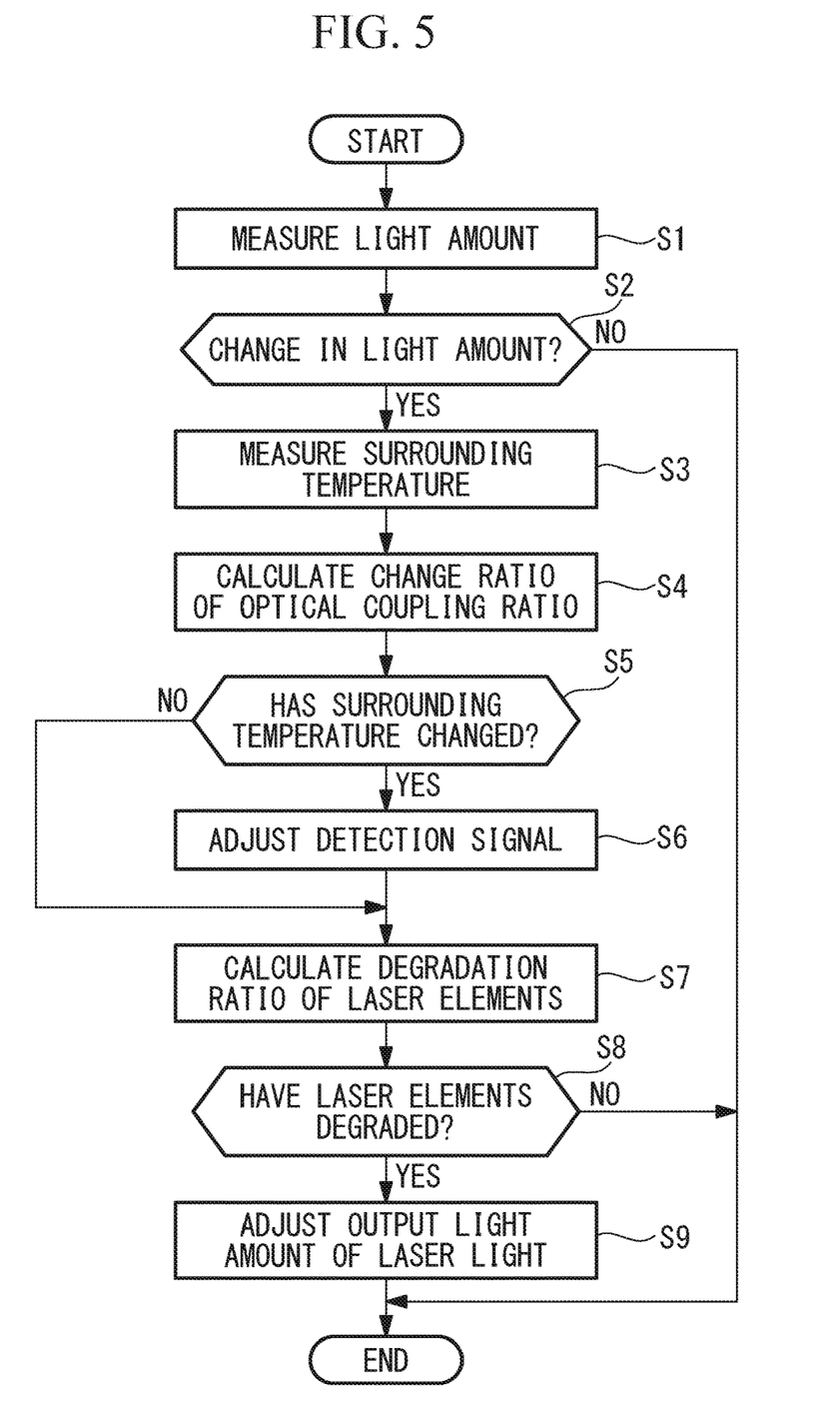
FIG. 5 is a flowchart for explaining operation of the optical scanning endoscope device in FIG. 1.

Next, operation of the thus-configured optical scanning endoscope device 1 will be described while referring to FIG. 5.

When the subject A is to be observed using the optical scanning endoscope device 1 according to this embodiment, control of the laser elements 9R, 9G, and 9B by the laser control unit 11 and supply of a voltage to the actuator 14 from the driving control unit 15 are initiated. As a result, the leading end of the optical fiber 13 is made to vibrate by the actuator 14 while R, G, and B laser light is supplied in a prescribed order from the light source unit 4 to the optical fiber 13, and the laser light radiated onto the subject A is scanned.

Laser light scattered from the subject A is received by the optical fiber 16 and detected by the light-detecting unit 6, and a detection signal is obtained. The detection signals are associated with positions along a scanning track of the laser light and an image of the subject A is thereby generated in the image-processing unit 7, and the image is displayed on the display 8.

Here, the light amount P3, which is part of the laser light incident on the optical fiber 13, is detected by the guided-light-amount detecting unit 23 (step S1) and a determination is made as to whether to adjust the emitted light amount P2 on the basis of the detected light amount P3 (step S2). When the detected light amount P3 has changed from the light amount at the reference temperature $T_0$ at the time of shipping (YES in step S2), next, the surrounding temperature $T_1$ is detected by the temperature-detecting unit 22 (step S3), the optical coupling ratios $\alpha(T_1)$ and $\alpha(T_0)$ at the reference temperature $T_0$ and the surrounding temperature $T_1$ are read out from storage unit 21, and the change ratio $\alpha(T_1)/\alpha(T_0)$ of the optical coupling ratio is calculated (step S4).

When there is a change in the surrounding temperature $T_1$ detected in step S3 from the reference temperature $T_0$ (YES in step S5), the detection signal is amplified on the basis of the calculated change ratio $\alpha(T_1)/\alpha(T_0)$ (step S6). On the other hand, when the surrounding temperature $T_1$ is equal to the reference temperature $T_0$ (NO in step S5), step S6 is not performed and the processing advances to the subsequent step S7.

Next, the degradation ratio $P1(t_1)/P1(0)$ of the laser elements 9R, 9G, and 9B is calculated from the detected light amount P3 and the change ratio $\alpha(T_1)/\alpha(T_0)$ of the optical coupling ratio (step S7), and when a reduction has occurred in the output light amount $P1(t_1)$ due to degradation of the laser elements 9R, 9G, and 9B (when the degradation ratio is less than 1) (YES in step S8), the driving current supplied to the laser elements 9R, 9G, and 9B from the laser control unit 11 is increased on the basis of the degradation ratio such that the output light amount $P1(t_1)$ becomes equal to the output light amount P1(0) at the time of shipping (step S9). On the other hand, when there is no reduction in the output light amount $P1(t_1)$ due to degradation (NO in step S8), step S9 is not executed.

As described above, there are two factors responsible for a reduction in the emitted light amount P2 from the optical fiber 13, namely, changes in temperature and degradation of the laser elements 9R, 9G, and 9B over time. According to this embodiment, a reduction in the emitted light amount P2 caused by a change in temperature is electrically compensated for by amplifying the detection signal and a reduction in the emitted light amount P2 caused by degradation of the laser elements 9R, 9G, and 9B over time is compensated for by increasing the driving current supplied to the laser elements 9R, 9G, and 9B. Thus, there is an advantage in that the load acting on the laser elements 9R, 9G, and 9B can be reduced by suppressing an increase in the driving current supplied to the laser elements 9R, 9G, and 9B and degradation of the laser elements 9R, 9G, and 9B can be suppressed.

Next, modifications of the optical scanning endoscope device 1 according to the above-described embodiment will be described.

First Modification

Figure 7:
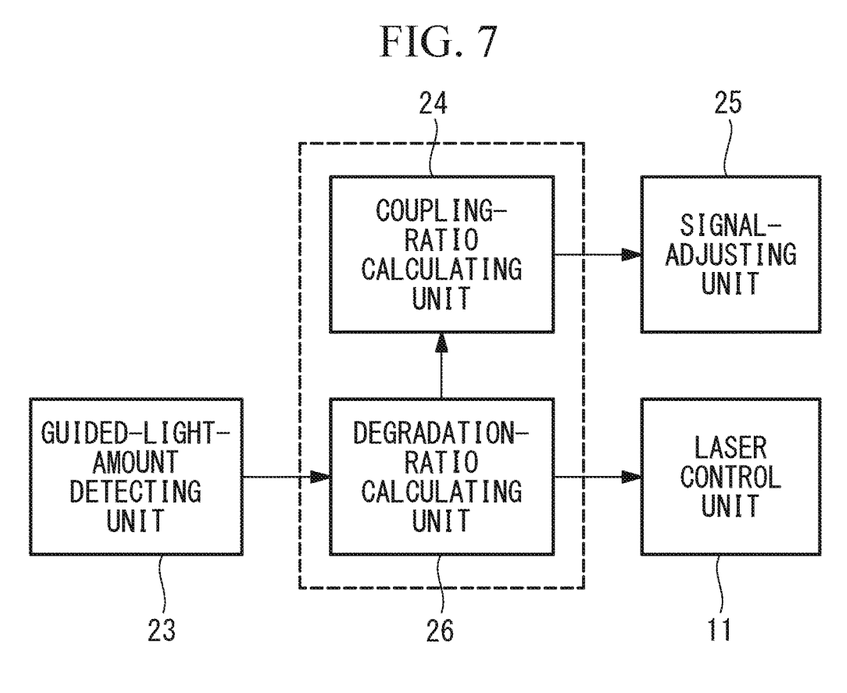
FIG. 7 is a diagram illustrating the flow of signals in a first modification of the optical scanning endoscope device in FIG. 1.

In a first modification, the degradation-ratio calculating unit 26 calculates the degradation ratio on the basis of an I-L characteristic (driving current vs. light output characteristic) that represents the relationship between the driving current and the output light amount of the laser elements 9R, 9G, and 9B instead of on the basis of the change ratio of the optical coupling ratio.

Figure 6:
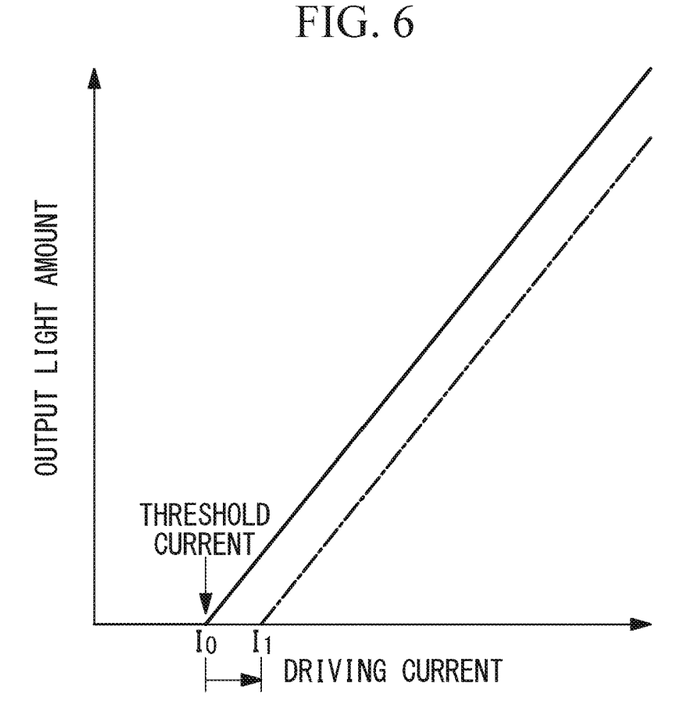
FIG. 6 is a graph illustrating an example of an I-L characteristic of a laser element.

The laser elements 9R, 9G, and 9B oscillate and generate laser light upon being supplied with a driving current of a magnitude greater than or equal to a current threshold and the output light amount of the laser elements 9R, 9G, and 9B linearly increases as the driving current increases. FIG. 6 illustrates an example of the relationship between a driving current I and an output light amount L (=P1). It is known that a current threshold $I_0$ increases due to degradation of the laser elements 9R, 9G, and 9B and that the output light amount L consequently decreases. Therefore, degradation of the laser elements 9R, 9G, and 9B can be detected from a change in the current threshold $I_0$.

A gradient $k=\Delta L/\Delta I$ of the I-L characteristic is substantially constant regardless of degradation of the laser elements 9R, 9G, and 9B. In addition, the current threshold is not affected by the surrounding temperature T and the optical coupling ratio $\alpha$. Therefore, a current threshold $I_1$ can be estimated from the value of the driving current supplied to the laser elements 9R, 9G, and 9B from the laser control unit 11, the detected light amount P3 detected by the guided-light-amount detecting unit 23, and the gradient k of the I-L characteristic, and the degradation ratio can be calculated from the calculated current threshold $I_1$. FIG. 7 illustrates the flow of signals in this modification.

Figure 8:
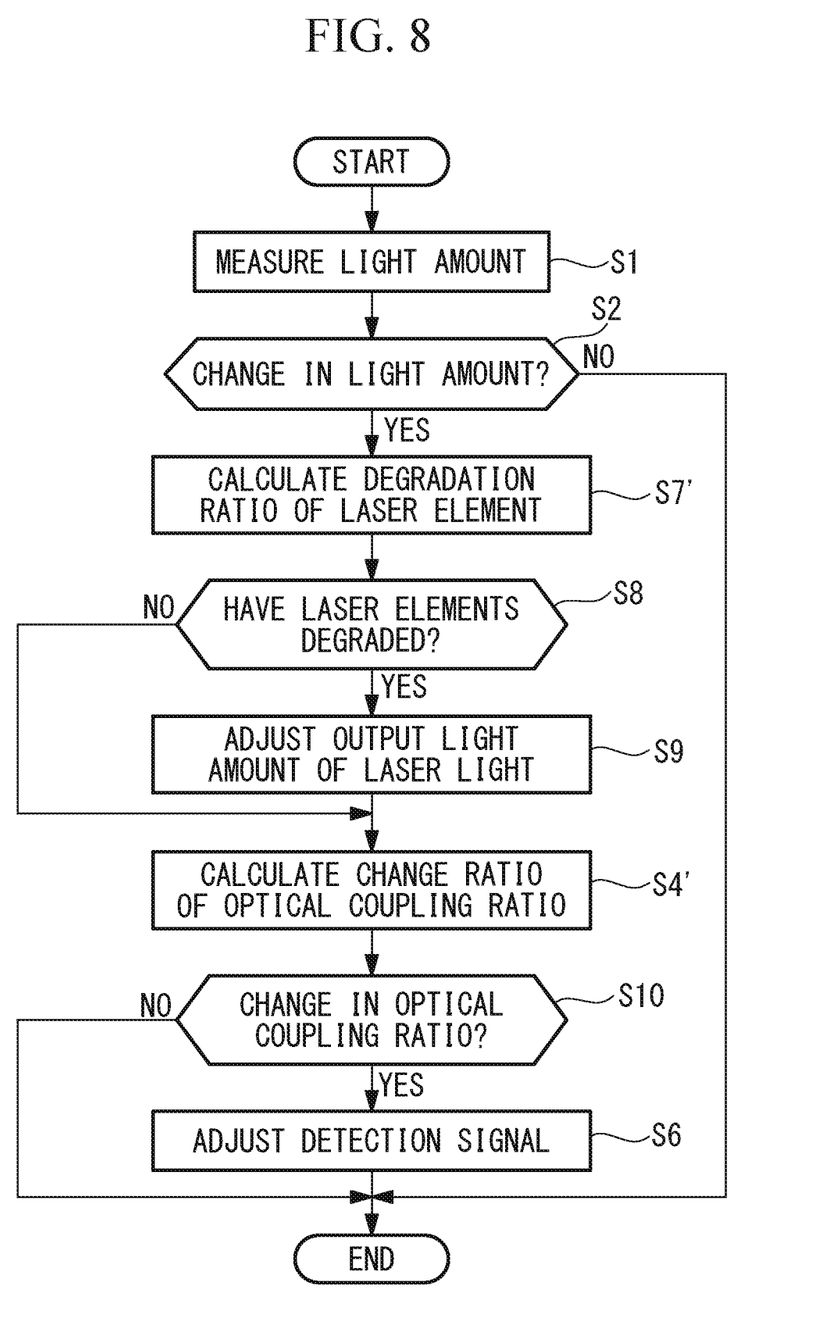
FIG. 8 is a flowchart for explaining operation of the first modification of the optical scanning endoscope device in FIG. 1.

Specifically, as illustrated in FIG. 8, the degradation-ratio calculating unit 26 calculates the current threshold $I_1$ from the I-L characteristic, reads out the initial current threshold $I_0$ and gradient k stored in the storage unit 21, and calculates the degradation ratio $\Delta L = k(I_1 - I_0)$ (step S7'). Therefore, the gradient k of the I-L characteristic and the initial current threshold $I_0$ are stored in the storage unit 21 prior to shipping.

When the degradation ratio $\Delta L$ is larger than 0 due to a reduction in the output light amount P1 of the laser elements 9R, 9G, and 9B (YES in step S8), the driving current supplied to the laser elements 9R, 9G, and 9B is increased on the basis of the degradation ratio $\Delta L$ (step S9). Next, the optical coupling ratio $\alpha$ is calculated from the degradation ratio $\Delta L$ calculated in step S7' and the detected light amount P3 (step S4'), and the detection signal is amplified.

According to this modification, the temperature-detecting unit 22 is not necessary, and therefore the device configuration can be simplified and the cost can be reduced.

Second Modification

Figure 9:
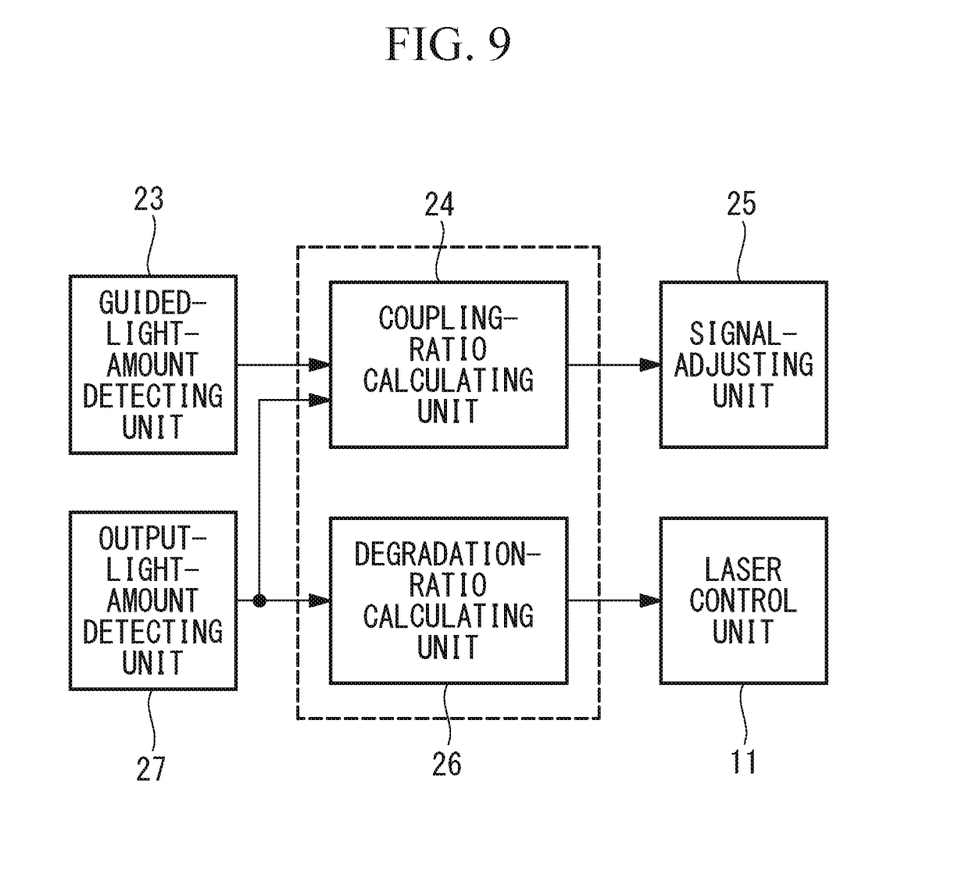
FIG. 9 is a diagram illustrating part of the configuration of and the flow of signals in a second modification of the optical scanning endoscope device in FIG. 1.

In a second modification, as illustrated in FIG. 9, an output-light-amount detecting unit 27, which detects the output light amount P1 of the laser light output from the laser elements 9R, 9G, and 9B, is further provided in the vicinity of the laser elements 9R, 9G, and 9B.

The degradation-ratio calculating unit 26 calculates the change ratio of the light amount $P1(t_1)$ detected by the output-light-amount detecting unit 27 with respect to the initial output light amount P1(0) as the degradation ratio $P1(t_1)/P1(0)$ of the laser elements 9R, 9G, and 9B. The coupling-ratio calculating unit 24 calculates the optical coupling ratio $\alpha(T_1)$ on the basis of formula (6) using the degradation ratio $P1(t_1)/P1(0)$ calculated by the degradation-ratio calculating unit 26 and the detected light amount $P3(t_1, T_1)$.

According to this modification, the degradation ratio is directly detected by detecting the output light amount $P1(t_1)$ of the laser elements 9R, 9G, and 9B. Thus, there is an advantage in that the accuracy with which the degradation ratio is detected can be improved.

Third Modification

In a third modification, the laser control unit 11 controls the output light amount of the laser elements 9R, 9G, and 9B by adjusting the temperature of the laser elements 9R, 9G, and 9B instead of adjusting the driving current or in conjunction with adjusting the driving current.

In addition to the driving current, the output light amount of the laser elements 9R, 9G, and 9B also depends on the temperature of the laser elements 9R, 9G, and 9B, and the output light amount increases as the temperature decreases. For example, the laser control unit 11 makes the output light amount increase by making the temperature of the laser elements 9R, 9G, and 9B decrease by controlling a temperature control element such as a Peltier element provided for the laser elements 9R, 9G, and 9B.

According to this modification, the temperature of the laser elements 9R, 9G, and 9B is reduced when the output light amount is increased, and therefore degradation of the laser elements 9R, 9G, and 9B can be further reduced.

Fourth Modification

In a fourth modification, the light source unit 4 operates using a continuous wave method in which R, G, B continuous wave laser light is output instead of a time division modulation method in which R, G, B pulsed laser light is sequentially output. Therefore, three light-detecting units 6 are provided so as to respectively correspond to the R, G, and B laser light beams. Each light-detecting unit 6 includes an APD having a multiplication factor that can be changed in accordance with the applied high voltage.

The signal-adjusting unit 25 sets the amplification factor of each light-detecting unit 6 on the basis of the reciprocal of the change ratio of the optical coupling ratio. Therefore, when a decrease has occurred in the emitted light amount P2 due to a change in temperature, a detection signal that has been amplified with a larger amplification factor so as to compensate for the decrease in the emitted light amount P2 is output from each light-detecting unit 6.

Thus, a detection signal can be adjusted over a wide range and without the generation of digital noise by adjusting the avalanche amplification factor.

In this modification, the change ratio of the optical coupling ratio may be individually calculated for each of the R, G, and B laser light beams and the APD amplification factor may be individually set for each of the R, G, and B colors. Thus, the white balance and color balance of an image can be adjusted in an analog manner by adjusting the APD amplification factor for each color, and therefore noise can be reduced compared with the case where the white balance and color balance are digitally adjusted.

Fifth Modification

In a fifth modification, the laser control unit 11 controls the output light amount P1 such that the reduction ratio of the output light amount P1 caused by degradation of the laser elements 9R, 9G, and 9B over time is constant.

A sudden reduction in the output light amount of the laser elements 9R, 9G, and 9B due to degradation will result in a sudden reduction in image quality and therefore is an issue that cannot be permitted, whereas a gentle reduction in image quality to the extent that observation is not hindered is permitted.

Therefore, a reduction in the output light amount of the laser elements 9R, 9G, and 9B that lies within a prescribed range (for example, a reduction of 5% within one year) is permitted, and the laser control unit 11 controls the output light amount so as to compensate for such a reduction by increasing the driving current only when the reduction in the output light amount exceeds this value. Thus, the load acting on the laser elements 9R, 9G, and 9B can be further reduced and degradation of the laser elements 9R, 9G, and 9B can be further suppressed.

The above-described embodiment also leads to the following invention.

An aspect of the present invention provides an optical scanning endoscope device that includes: a laser element that outputs laser light; an optical fiber that guides the laser light output from the laser element and emits the laser light toward a subject; a guided-light-amount detecting unit that detects a guided light amount of the laser light guided by the optical fiber; a light-detecting unit that detects light generated at the subject due to radiation of the laser light and outputs a detection signal; a coupling-ratio calculating unit that calculates an optical coupling ratio between the laser element and the optical fiber on the basis of the guided light amount detected by the guided-light-amount detecting unit; a degradation-ratio calculating unit that calculates a degradation ratio of the laser element on the basis of the guided light amount detected by the guided-light-amount detecting unit; a signal-adjusting unit that adjusts a magnitude of the detection signal on the basis of the optical coupling ratio calculated by the coupling-ratio calculating unit; and an output-light-amount adjusting unit that adjusts an output light amount of the laser light output from the laser element on the basis of the degradation ratio calculated by the degradation-ratio calculating unit.

According to this aspect, the laser light output from the laser element is radiated toward the subject via the optical fiber and observation light generated at the subject is detected by the light-detecting unit, and thus the observation light can be observed.

In this case, the guided light amount of the laser light in the optical fiber decreases when the optical coupling ratio between the laser element and the optical fiber decreases due to a change in the use environment such as the surrounding temperature. The coupling-ratio calculating unit calculates the optical coupling ratio on the basis of the guided light amount detected by the guided-light-amount detecting unit, and the signal-adjusting unit adjusts the magnitude of an observation light detection signal on the basis of the optical coupling ratio so as to amplify the detection signal when the optical coupling ratio has decreased. Thus, of a reduction amount of the emitted light amount of the laser light emitted from the optical fiber, a reduction amount arising from an environmental change such as the surrounding temperature is compensated for.

In addition, the guided light amount of laser light in the optical fiber decreases when the output light amount of the laser element decreases due to degradation of the laser element over time. The degradation-ratio calculating unit calculates the degradation ratio of the laser element on the basis of the guided light amount detected by the guided-light-amount detecting unit, and the output-light-amount adjusting unit adjusts the output light amount on the basis of the degradation ratio so as to increase the output light amount of the laser element when the output light amount has decreased. Thus, of the reduction amount of the emitted light amount of the laser light emitted from the optical fiber, a reduction amount arising from degradation of the laser element over time is compensated for.

Thus, a reduction in the emitted light amount that occurs together with degradation of the laser element is compensated for by increasing the output light amount of the laser element and a reduction in the emitted light amount arising from other factors is compensated for by adjusting the detection signal, and as a result the light amount of the laser light emitted from the optical fiber can be adjusted so as to be constant while suppressing degradation of the laser element.

The optical scanning endoscope device of the above-described aspect may further include: a temperature-detecting unit that detects a surrounding temperature of the laser element; and a storage unit that stores a relationship between the surrounding temperature of the laser element and the optical coupling ratio. The coupling-ratio calculating unit may calculate the optical coupling ratio on the basis of the surrounding temperature detected by the temperature-detecting unit and the relationship stored in the storage unit, and the degradation-ratio calculating unit may calculate the degradation ratio from optical coupling ratio calculated by the coupling-ratio calculating unit and the guided light amount detected by the guided-light-amount detecting unit.

With this configuration, the optical coupling ratio at the detected surrounding temperature can be calculated by referring to the relationship between the surrounding temperature and optical coupling ratio stored in the storage unit. Furthermore, since the optical coupling ratio, the output light amount, and the guided light amount are in a fixed relationship with each other, the degradation ratio can be calculated from the calculated optical coupling ratio and the guided light amount.

The optical scanning endoscope device of the above-described aspect may further include: a storage unit that stores a relationship between the magnitude of a driving current supplied to the laser element and the output light amount of the laser element. The degradation-ratio calculating unit may calculate the degradation ratio on the basis of the guided light amount detected by the guided-light-amount detecting unit and the relationship stored in the storage unit, and the coupling-ratio calculating unit may calculate the optical coupling ratio from the degradation ratio calculated by the degradation-ratio calculating unit and the guided light amount detected by the guided-light-amount detecting unit.

In a driving current versus light output characteristic of the laser element that represents the relationship between the driving current and the output light amount, a current threshold increases as degradation of the laser element progresses. It is possible to calculate the degradation ratio of the laser element without the need for an additional sensor by obtaining an increase amount of the current threshold from the guided light amount detected by the guided-light-amount detecting unit and the driving current versus light output characteristic. Furthermore, since the degradation ratio, the optical coupling ratio, and the guided light amount are in a fixed relationship with each other, the optical coupling ratio can be calculated from the calculated degradation ratio and the guided light amount.

The optical scanning endoscope device of the above-described aspect may further include: an output-light-amount detecting unit that detects the output light amount output from the laser element. The degradation-ratio calculating unit may calculate the degradation ratio on the basis of the output light amount detected by the output-light-amount detecting unit, and the coupling-ratio calculating unit may calculate a change ratio of the optical coupling ratio from the output light amount detected by the output-light-amount detecting unit and the guided light amount detected by the guided-light-amount detecting unit.

With this configuration, the degradation ratio of the laser element can be directly calculated from the output light amount detected by the output-light-amount detecting unit. Furthermore, since the degradation ratio, the optical coupling ratio, and the guided light amount are in a fixed relationship with each other, the optical coupling ratio can be calculated from the calculated degradation ratio and the guided light amount.

In the above-described aspect, the output-light-amount adjusting unit may adjust the output light amount such that a reduction ratio of the output light amount caused by degradation of the laser element is constant.

With this configuration, degradation of the laser element can be further suppressed.

In the above-described aspect, the output-light-amount adjusting unit may adjust at least one of a driving current supplied to the laser element and a temperature of the laser element.

The output light amount of the laser element can be adjusted over a wide range by adjusting the driving current. In addition, the output light amount can be increased while suppressing degradation of the laser element by reducing the temperature of the laser element.

REFERENCE SIGNS LIST 1 optical scanning endoscope device
2 scope
3 casing
4 light source unit
5 optical scanning unit
6 light-detecting unit
7 image-processing unit
8 display
9R, 9G, 9B laser element
10 coupling unit
11 laser control unit (output-light-amount adjusting unit)
12 coupling element
13 optical fiber
14 actuator
15 driving control unit
16 optical fiber
21 storage unit
22 temperature-detecting unit
23 guided-light-amount detecting unit
24 coupling-ratio calculating unit
25 signal-adjusting unit
26 degradation-ratio calculating unit
27 output-light-amount detecting unit

The invention claimed is:

1. An optical scanning endoscope device comprising:
a laser element configured to output laser light;
an optical fiber configured to guide the laser light output from the laser element and emit the laser light toward a subject; and
a processor comprising hardware, the processor being configured to:
receive a detected guided light amount of the laser light guided by the optical fiber;
receive a detection signal generated based on a detected light generated at the subject due to radiation of the laser light;
calculate an optical coupling ratio between the laser element and the optical fiber on the basis of the detected guided light amount;
calculate a degradation ratio of the laser element on the basis of the detected guided light amount;
adjust a magnitude of the detection signal on the basis of the optical coupling ratio calculated; and
adjust an output light amount of the laser light output from the laser element on the basis of the degradation ratio calculated.

2. The optical scanning endoscope device according to claim 1, further comprising:
a storage that stores a relationship between a detected surrounding temperature of the laser element and the optical coupling ratio;
wherein the processor is configured to:
calculate the optical coupling ratio on the basis of the detected surrounding temperature and the relationship stored in the storage; and
calculate the degradation ratio from the optical coupling ratio calculated and the detected guided light amount.

3. The optical scanning endoscope device according to claim 1, further comprising:
a storage configured to store a relationship between a magnitude of a driving current supplied to the laser element and the output light amount of the laser light output from the laser element, wherein the processor is configured to:

calculate the degradation ratio on the basis of the detected guided light amount and the relationship stored in the storage; and calculate the optical coupling ratio from the degradation ratio calculated and the detected guided light amount.

4. The optical scanning endoscope device according to claim 1, wherein the processor is configured to:

receive a detected output light amount of the laser light output from the laser element;

calculate the degradation ratio on the basis of the detected output light amount of the laser light output from the laser element; and calculate a change ratio of the optical coupling ratio from the detected output light amount of the laser light output from the laser element and the detected guided light amount.

5. The optical scanning endoscope device according to claim 1, wherein the processor is configured to adjust the output light amount such that a reduction ratio of the output light amount caused by degradation of the laser element is constant.

6. The optical scanning endoscope device according to claim 1, wherein the processor is configured to adjust at least one of a driving current supplied to the laser element and a temperature of the laser element, to adjust the output light amount of the laser light output from the laser element.

* * * * *